(12) United States Patent
Palm-Plessmann et al.

(10) Patent No.: US 8,180,127 B2
(45) Date of Patent: May 15, 2012

(54) METHOD AND IMAGE EVALUATION SYSTEM FOR PREPARATION OF MEDICAL 2D OR 3 D DATA

(75) Inventors: Ulrike Palm-Plessmann, Fuerth (DE); Marcus Thaele, Stegaurach (DE)

(73) Assignee: Siemens Aktiengesellschaft, Munich (DE)

( * ) Notice: Subject to any disclaimer, the term of this patent is extended or adjusted under 35 U.S.C. 154(b) by 836 days.

(21) Appl. No.: 12/201,250

(22) Filed: Aug. 29, 2008

(65) Prior Publication Data

US 2009/0060302 A1    Mar. 5, 2009

(30) Foreign Application Priority Data

Aug. 30, 2007   (DE) .......................... 10 2007 041 108

(51) Int. Cl.
  *G06K 9/00* (2006.01)
(52) U.S. Cl. ...................................................... 382/128
(58) Field of Classification Search .................... 382/128
See application file for complete search history.

(56) References Cited

U.S. PATENT DOCUMENTS

| | | | |
|---|---|---|---|
| 6,658,080 B1* | 12/2003 | Poole et al. | 378/4 |
| 2005/0228250 A1 | 10/2005 | Bitter et al. | |
| 2006/0079743 A1 | 4/2006 | Ferrant et al. | |
| 2009/0087065 A1* | 4/2009 | DaSilva et al. | 382/131 |

* cited by examiner

*Primary Examiner* — Clayton E LaBalle
*Assistant Examiner* — Dennis Hancock
(74) *Attorney, Agent, or Firm* — Schiff Hardin LLP

(57) ABSTRACT

In a method and system to prepare medical 2D or 3D data, in particular 2D or 3D image data acquired by means of computed tomography, a data set composed of medical 2D or 3D data is segmented with predeterminable first segmentation parameters, so a first data set with segmented data and a second data set with data complementary to the first data set are generated and stored. Predeterminable color or grey value tables (known as presets) are provided that respectively associate colors or grey values with individual data value ranges. Respective presets are automatically associated with the first data set and the second data set. At an output unit, at least one slice or volume image of the first and/or second data set is presented as a resulting image/resulting images in colors/grey scales according to the associated presets.

18 Claims, 2 Drawing Sheets

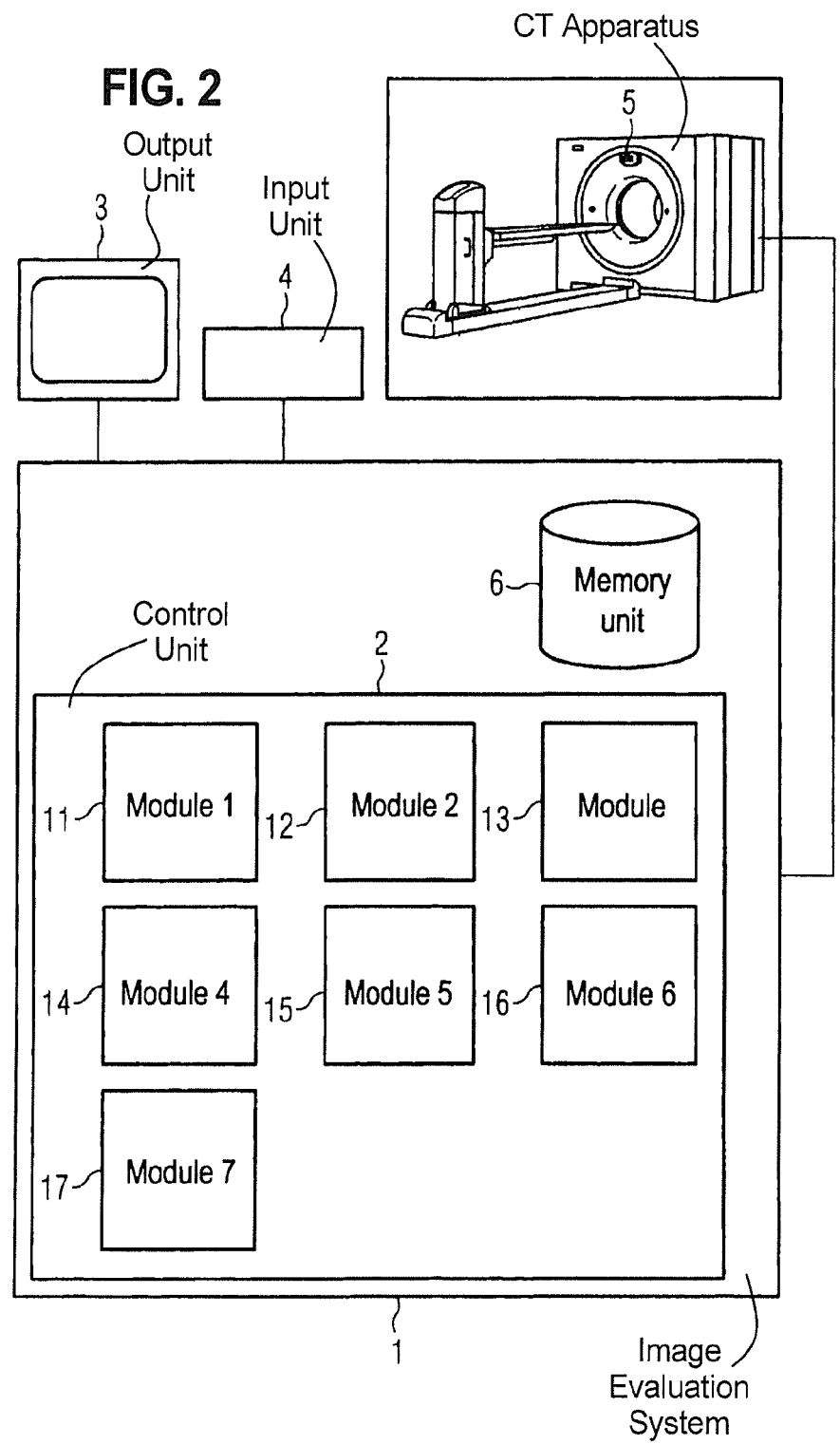

METHOD AND IMAGE EVALUATION SYSTEM FOR PREPARATION OF MEDICAL 2D OR 3D DATA

BACKGROUND OF THE INVENTION

1. Field of the Invention

The present invention concerns a method as well as an image evaluation system for preparation of medical 2D or 3D data, in particular of 2D or 3D image data acquired by means of computed tomography.

2. Description of the Prior Art 2D and/or 3D data in the medical field are acquired as the result of radiographic methods such as, for example, computed tomography, mammography, angiography, x-ray inspection technology or comparable methods. In these methods, the representation of the attenuation of an x-ray along its path from the radiation source (x-ray source) to the detector system (x-ray detector) ensues in a projection image. This attenuation is caused by the irradiated materials along the beam path, such that the attenuation can also be understood as a linear integral across the coefficients of all volume elements (voxels) along the beam path. In x-ray computed tomography (CT), it is possible by reconstruction methods to back-calculate the attenuation coefficients $\mu$ of the individual voxels from the projected attenuation data, and therefore to achieve a significantly more sensitive examination compared to consideration of the individual projection images.

Instead of the attenuation coefficients $\mu$, a value that is normalized to the attenuation coefficients of water (known as the CT count) is used to show the attenuation distribution. This is calculated from a current attenuation coefficient $\mu$ (determined by measurement) according to the following equation:

$$C = 1000 * \frac{\mu - \mu_{H_2O}}{\mu_{H_2O}} (HU)$$

with the CT count C in Hounsfield units (HU). A value $C_{H_2O}=0$ HU results for water and a value $C_L=-1000$ HU results for air. Since both representations can be transformed into one another, and thus are equivalent, in the following the general terms attenuation value or attenuation coefficient designate both the attenuation coefficients $\mu$ and the CT value.

Modern x-ray computed tomography (CT) apparatuses are used for the acquisition, evaluation and presentation of the three-dimensional attenuation distribution in the medical field. A CT apparatus typically has a radiation source that directs a collimated, pyramidal or fan-shaped radiation beam through the examination subject (for example a patient) onto a detector system constructed from multiple detector elements. Depending on the design of the CT apparatus, the radiation source and the detector system are mounted, for example, on a gantry or on a C-arm that can be rotated around a system axis with an angle $\phi$. Furthermore, a support device for the examination subject is provided that can be shifted or moved along the system axis. During the acquisition, each detector element of the detector system that is struck by the radiation produces a signal that represents a measure of the total transparency of the examination subject for the radiation emanating from the radiation source on its path to the detector system, i.e., the corresponding radiation attenuation. The set of output signals of the detector elements of the detector system that is acquired for a specific position of the radiation source is designated as a projection. The position, starting from which the radiation beam passes through the examination subject, is continuously altered as a result of the rotation of the gantry/C-arm. A scan thereby encompasses a number of projections that are acquired at various positions of the gantry/C-arm and/or various positions of the support device. Differentiation is made between sequential scan methods and spiral scan methods.

A two-dimensional slice image of a slice of the examination subject can be reconstructed on the basis of the data set generated in a scan. The quantity and quality of the measurement data acquired during a scan depend on the employed detector system. Multiple slices can be acquired simultaneously with a detector system that has an array composed of multiple rows and columns of detector elements. Detector systems with 256 or more rows are known today. The generated scan data and/or image data are typically prepared and visualized with an image evaluation system (for example a post-processing workstation).

SUMMARY OF THE INVENTION

An object of the present invention is to provide a method for preparation of medical 2D or 3D data, in particular of 2D or 3D image data acquired by means of computed tomography. Furthermore, it is an object of the invention to provide an image evaluation system with which the method according to the invention can be executed.

The method according to the invention to prepare medical 2D or 3D data, in particular 2D or 3D image data acquired by means of computed tomography, includes the following steps.

In a first step, a data set with medical 2D or 3D data (for example a CT volume data set or a 3D data set from a magnetic resonance tomograph) is prepared. Segmentation of the prepared data set with predeterminable first segmentation parameters ensues in a second step, resulting in a first data set with segmented data and a second data set with data complementary to the first data set being generated and stored.

"Segmentation" is a well-known procedure in digital image processing and designates the generation of regions that are connected in terms of content by aggregation of adjacent pixels or voxels of the 2D or 3D data set corresponding to predetermined homogeneity criteria. The homogeneity criteria can in turn be predetermined as specific segmentation parameters. A "complete segmentation" means that at least one segment is associated with each pixel. At most one segment is associated with each pixel in an overlap-free segmentation. In a complete and overlap-free segmentation, exactly one segment is thus associated with each pixel. Segmentation is described as contiguous when each segment forms a contiguous region.

Many methods are known for automatic segmentation. In principle, they are categorized into pixel-oriented, edge-oriented and region-oriented methods. The most widespread method category is the threshold method. Typically, threshold methods binarize an initial image data set, meaning that exactly two segments (data sets or layers) are thereby generated. A data set with the sought subjects (segmented data) and a data set with the background (i.e. the data complementary to the first data set) are most frequently formed. The association with both segments (for example by an association of the values 0 and 1) typically occurs by to a comparison of the grey value g of the pixel in question with a pre-established threshold t. The resulting image thus can be calculated with a very small computational effort, since only a simple comparison operation must be implemented per pixel. The associated calculation rule of the image $T_g$ is:

$$T_g(g) = \begin{cases} 0 & \text{if } g < t \\ 1 & \text{if } g \geq t \end{cases}$$

Threshold methods are complete segmentation methods, meaning that it is mandatory that a segment is associated with each pixel. They are likewise overlap-free, meaning that multiple segments are not associated with any pixel. In contrast to many other segmentation methods, threshold methods do not form any contiguous segments. It is conceivable and often even desired that multiple spatially separate subjects in the image that have a similar brightness value are merged into one segment.

A typical example for the application of segmentation in CT image data sets is the procedure known as the "bone removal" method in which the bones that exhibit very similar brightness values in the x-ray image data from the original CT image data set are "extracted" from the remaining tissue.

The provision of predeterminable color or grey value tables (known as presets) that respectively associate colors or grey values with data value ranges and/or individual data values typically occurs as a data file in a third step of the method according to the invention. The association of the color values or grey values with the data value ranges or data values is in principle dependent on the object (goal) of the image data evaluation and on the available image data. If specific subjects (for example vessels, muscle fibers, bones, etc.) should be shown, respective presets for these are predetermined with which the structures or tissue portions of interest are emphasized particularly well, such that they can differentiated from one another.

A preset is automatically (i.e. controlled by a program or software) associated with the first data set and with the second data set in a fourth step. In a preferred embodiment of the method, the automatic association of the presets ensues depending on the selected segmentation parameters. In a fifth method step, the presentation of at least one slice or volume image of the first and/or second data set ensues at an output unit (for example on a monitor) as a resulting image/resulting images in colors/grey scales according to the associated presets.

In some cases, the quality of the segmentation is not optimal. In these cases a better segmentation method can be selected or the results can be optimized in that a post-processing follows. Both can occur both automatically and manually. In a further preferred embodiment of the method, segmentation of the first or second data set with segmentation parameters modified relative to the second step ensues in an optional sixth step, wherein a third data set with segmented data and a fourth data set with data complementary to the third data set are generated. The third and fourth data sets are advantageously stored.

In an additional advantageous embodiment of the method, a seventh method step follows wherein the first and/or second data set is set against the third and/or fourth data set so that a corrected first and/or second data set is obtained as a result. The corrected first and/or second data set is advantageously stored.

One problem of many segmentation algorithms is the tendency for alternating exposure within the image. This can lead to the situation that one image part is always correctly segmented but the segmentation is unusable in the other image parts. Brightness differences can advantageously be compensated with a pre-processing, for example by applying a shading correction.

In a further preferred embodiment of the method, the first and/or second data set are replaced by the corrected first and/or second data set so that, after ending the seventh method step, the method can be executed again beginning with the third method step for the corrected first and/or second data set. Presets are thereby provided and automatically associated for the corrected first and/or second data set, and at least one slice image or volume image of the corrected first and/or second data set is displayed on the output unit as a result image/result images.

The data sets generated in the course of the method are preferably stored on one or more permanent storage media. Furthermore, a manual change of image presentation parameters (such as opacity, color, definition, edge production etc.) for the presentation of the result images as well as a manual input and/or change of the presets by a user can advantageously ensue by means of an input unit.

An image evaluation system for preparation of medical 2D or 3D data (in particular of 2D or 3D image data acquired by means of computed tomography) has an output unit, an input unit, a memory unit and a control unit configured to execute all embodiments of the method described above.

In an advantageous embodiment, the control unit has a first module with which a medical 2D or 3D data set to be prepared can be provided, a second module with which the data set can be segmented with predeterminable segmentation parameters, so a first data set with segmented data and a second data set with data complementary to the first data set are generated and stored in a memory unit, a third module with which predeterminable color or grey value tables (known as presets) that associate colors or grey values with respective individual display value intervals and/or data values can be provided, a fourth module with which a preset can respectively be automatically associated with the first data set and second data set, and a fifth module with which causes a presentation at the output unit of at least one slice or volume image of the first and/or second data set as a resulting image/resulting images in colors/grey scales according to the associated presets. The second module for specification of the segmentation parameters is advantageously connected with the input unit. Furthermore, the second module can have a memory to store the predeterminable segmentation parameters or a data connection to the memory unit. In the latter case the segmentation parameters are stored in the memory unit.

In a further embodiment of the image evaluation system, the third module for specification of the presets is connected with the input unit. The third module can include a memory to store the predeterminable presets.

In a further embodiment, the fourth module and the second module are connected with one another such that the segmentation parameters can be transmitted from the second module to the fourth module, wherein in the fourth module a preset can respectively be associated with the first data set and second data set dependent on the transmitted segmentation parameters.

In another embodiment, the control unit has a sixth module with which the first or second data set can be segmented with second segmentation parameters, so a third data set with segmented data and a fourth data set with data complementary to the third data set can be generated and stored. The second and first segmentation parameters are different from one another. Furthermore, the sixth module and the second module can be identical.

Moreover, the control unit can have a seventh module with which the first and/or second data set can be set against the third and/or fourth data set such that a corrected first and/or second data set can be generated. The seventh module is advantageously connected with the memory unit, such that the corrected first and/or second data set can be stored in a memory unit (for example a permanent storage medium).

Image presentation parameters such as opacity, color, definition, edge formation, etc. can be manually modified by a user by entries into the input unit.

BRIEF DESCRIPTION OF THE DRAWINGS

FIG. 2 is a block diagram of an image evaluation system according to the invention.

DESCRIPTION OF THE PREFERRED EMBODIMENTS

Figure 1A:
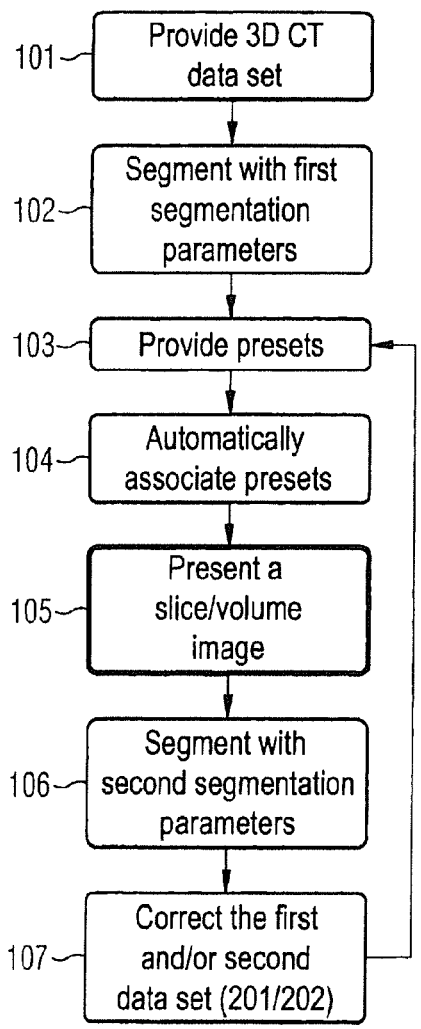
FIG. 1A is a flowchart that shows the sequence of individual method steps of a preferred embodiment of the present method.
Figure 1B:
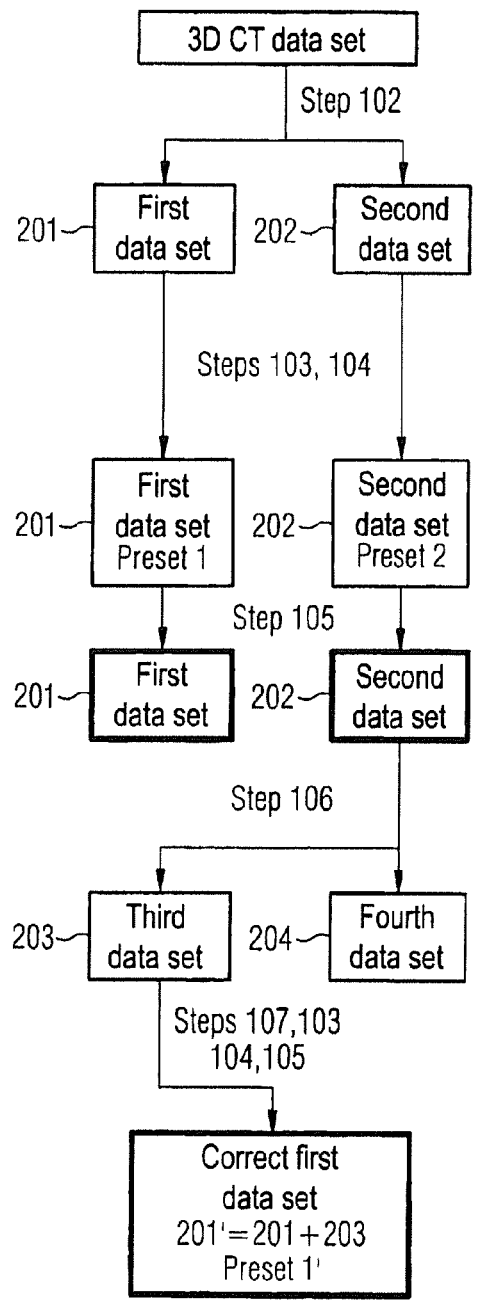
FIG. 1B is a schematic illustration of the data sets generated during the method presented in FIG. 1A.

The sequence of method steps of a preferred embodiment of the inventive method is shown in FIG. 1A. The method can be executed on an image evaluation unit 1 with an output unit 3, an input unit 4, a memory unit 6 and a control unit 2. The method proceeds through Steps 101-107, followed by Steps 103-105 again. The data sets generated during the method workflow shown in FIG. 1B, such that both the individual method steps and their respective effect on the processed data can be tracked according to FIGS. 1A and 1B. The individual method steps are subsequently described separately.

A 3D image data set 200 generated by means of a computed tomography apparatus 5 is provided in Step 101. This typically ensues by transfer of the image data set 200 to be prepared and to be presented from the CT apparatus 5 to the memory unit 6 of the image evaluation system 1.

Segmentation of the data set 200 with predetermined first segmentation parameters ensues in Step 102. The segmentation parameters are presently selected such that the bone portions are extracted from the 3D image data set (bone removal). A first data set 201 with segmented data (i.e. with the tissue without bones) and a second data set 202 with data complementary to the first data set 201 (i.e. a bone data set) are generated in this method step 102 and stored in the memory unit 6.

Presets previously generated and stored in the memory unit 6 are provided in Step 103 and automatically associated with the first and second data set 201/202 in Step 104. The association thereby advantageously occurs dependent on the previously occurred segmentation or, respectively, on the segmentation parameters thereby used. Segmentation parameters that (as mentioned in the preceding) correspond to a bone removal process have presently been selected in Step 102. A first data set 201 with tissue without bones and a second data set 202 with bones without tissue were thereby generated as a result of the segmentation 102. A preset that is optimally suited to present tissue images without bones and an additional preset that is optimally suited to present bone images without tissue are now automatically selected from the prepared presets by the control unit 2.

After the respective association of presets 1 and 2 with the data sets 201 and 202, the data sets are presented in the result as three-dimensional images in a VR technique (volume rendering technique) on the display unit 3 in method step 105. The result images can be mixed in or out by the user. The user furthermore has the possibility to manually modify the result images, i.e. modifications of the opacity, the ratio of the display from the first result image to second result image, the color, the definition or even the edge formation or the respective light sources.

If the user, based on the display of the result image(s), realizes that the bone removal in Step 102 is incomplete or has occurred incorrectly, in Step 106 the user has the possibility to implement an additional bone removal for the data set 202, i.e. a segmentation of the data set 202 with segmentation parameters optimized relative to Step 102. The modification of the segmentation parameters ensues either automatically (i.e. controlled by software) or manually by the user via the input unit. A third data set 203 with segmented data and a fourth data set 204 with data complementary to the third data set 203 arise due to this re-segmentation. Naturally, the fourth data set 204 could also be segmented instead of the third data set 203.

Depending on the object of the image evaluation and errors that occurred, an offsetting of first and/or second data set 201/202 with the third and/or fourth data set 203/204 ensues in Step 107 in order to obtain as a result a corrected first and/or second data set. In the simplest case (as can presently be learned from FIG. 1B), the corrected first data set 201' (and therefore an optimized result image of the bone removal) results via addition of data sets 201 and 203.

Steps 103 through 105 are executed again for the corrected first data set 201' generated in Step 107, wherein a different preset 1' can be associated with the corrected data set 201' in Step 104 due to the second segmentation 106. The method is ended with the display of the corrected first data set 201' in Step 105.

Naturally, a new (third) segmentation with Step 106 can also occur for the corrected data set 201', such that the method enables an additional optimization of image presented in a type of method loop.

An image evaluation system 1 is presented in a schematic manner in FIG. 2. The image evaluation system 1 has an output unit 3, an input unit 4, a data connection to a CT apparatus 5, a memory unit 6 and a control unit 2. The control unit 2 has a first module 11 that provides a 2D or 3D data set 200 to be prepared and a second module 12 with which the data set 200 is segmented with predeterminable segmentation parameters. A first data set 201 with segmented data and a second data set 202 with data complementary to the first data set 201 can be generated and stored in the memory unit 6. The control unit 2 also has a third module 13 with which predeterminable color or grey value tables (known as presets) are provided that respectively associate colors or grey values with individual data value intervals and/or data values, and a fourth module 14 with which presets are respectively be automatically associated with the first data set and second data set 201/202. The control unit 2 further includes a fifth module 15 that causes at least one slice or volume image of the first and/or second data set to be presented as a resulting image/resulting images in colors/grey scales on the output unit 4 according to the associated presets. The control unit 2 has a sixth module 16 with which the first or second data set 201/202 is segmented with modified segmentation parameters, wherein a third data set 203 with segmented data and a fourth data set 204 with data complementary to the third data set 203 are generated and stored. The control unit 2 has a seventh module 17 with which the first and/or second data set 201/202 are offset against the third and/or fourth data set 203/204, such that a corrected first and/or second data set 201'/202' is generated.

The method according to the invention and the image evaluation system according to the invention enable an individual, optimal visualization of medical 2D or 3D data by automatically associated presets. Furthermore, possibilities for correction of automatic segmentation processes are provided. Overall, the present subject matter of the invention corresponds to the requirements of a workflow-oriented clinical routine, in particular to the requirements according to standardized workflows in the presentation of medical image data in order to ensure that the resulting images are comparable with one another.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to prepare medical 2D or 3D data, comprising the steps of:
   (a) providing a data set comprised of medical 2D or 3D data;
   (b) segmenting the data set with predeterminable first segmentation parameters, to obtain and store a first data set with segmented data and a second data set with data complementary to the first data set;
   (c) segmenting the first data set or second data set with segmentation parameters modified relative to step (b), to generate a third data set with segmented data and a fourth data set with data complementary to the third data set, and offsetting the first data set and/or second data set against the third data set and/or fourth data, to obtain a corrected first data set and/or second data set;
   (d) providing presets comprised of predetermined color or grey value tables that respectively associate colors or grey values with individual data value ranges;
   (e) automatically associating the preset with the first data set and second data set, respectively; and
   (f) presenting at an output unit at least one slice or volume image of the first and/or second data set as a resulting image/resulting images in colors/grey scales according to the associated presets.

2. A method according to claim 1, comprising:
   automatically associating the presets in step (d) dependent on selected segmentation parameters.

3. A method according to claim 1, comprising storing the third data set and/or fourth data set.

4. A method according to claim 1, comprising storing the corrected first and/or second data set.

5. A method according to claim 1, comprising replacing the first data set and/or second data set with the corrected first data set and/or second data set.

6. A method according to claim 1, comprising storing the generated data sets on a permanent storage medium.

7. A method according to claim 1, comprising manually modifying image presentation parameters selected from the group consisting of opacity, color, definition, and edge formation for presenting said at least one slice or volume image in step (f).

8. A method according to claim 1, comprising manually modifying the presets.

9. An image evaluation system to prepare medical 2D or 3D data, comprising:
   a first module configured to provide a data set comprised of medical 2D or 3D data;
   a second module configured to segment the data set with predeterminable first segmentation parameters, in order to obtain and store a first data set with segmented data and a second data set with data complementary to the first data set;
   a third module configured to segment said first data set or said first data set with second segmentation parameters, to produce a third data set comprised of segmented data and a fourth data set with data complementary to the segmented data in the third data set, and to sore said third data set and said fourth data set;
   a fourth module configured to offset said first data set and/or said second data set against said third data set and/or said fourth data set, respectively, to produce a corrected first data set and/or a corrected second data set;
   a fifth module configured to provide presets comprised of predetermined color or grey value tables that respectively associate colors or grey values with individual data value ranges;
   a sixth module configured to automatically associate the presets with the corrected first data set and/or second data set, respectively; and
   a seventh module configured to present, at an output unit, at least one slice or volume image of the corrected first and/or second data set as a resulting image/resulting images in colors/grey scales according to the associated presets.

10. An image evaluation system as claimed in claim 9, comprising an input unit connected to said second module allowing manual specification of said segmentation parameters.

11. An image evaluation system as claimed in claim 9 comprising a memory accessible by said second module in which said predeterminable segmentation parameters are stored.

12. An image evaluation system as claimed in claim 9 comprising an input unit connected to said fifth module allowing manual specification of said presets.

13. An image evaluation system as claimed in claim 9 comprising a memory accessible by said fifth module in which said predeterminable presets are stored.

14. An image evaluation system as claimed in claim 9 wherein said second module and said sixth module are in communication with each other to allow transfer of said segmentation parameters to said sixth module, and wherein said sixth module is configured to associate respective presets with said first data set and said second data set dependent on the transferred segmentation parameters.

15. An image evaluation system as claimed in claim 9 wherein said second module comprises said third module and said fourth module.

16. An image evaluation system as claimed in claim 9 comprising a memory unit accessible by said seventh module in which the corrected first data set and/or the corrected second data set are stored.

17. An image evaluation system as claimed in claim 16 wherein said memory unit is a permanent storage medium.

18. An image evaluation system as claimed in claim 9 comprising an input unit in communication with said seventh module allowing manual selection of image presentation parameters for presentation of said at least one slice or volume image at said output unit, selected from the group consisting of color, definition, and edge formation.

* * * * *